US011844694B2

(12) United States Patent
Anderson et al.

(10) Patent No.: US 11,844,694 B2
(45) Date of Patent: Dec. 19, 2023

(54) SIMPLIFIED COAXIAL SHAFT DESIGN DELIVERY SYSTEM AND IMPLANT FOR MITRAL VALVE ANNULUS REDUCTION

(71) Applicant: Boston Scientific Scimed, Inc., Maple Grove, MN (US)

(72) Inventors: James M. Anderson, Corcoran, MN (US); Joshua M. Inouye, Maple Grove, MN (US); Graham Krumpelmann, Stillwater, MN (US); John M. Edgell, Plymouth, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 332 days.

(21) Appl. No.: 17/125,156

(22) Filed: Dec. 17, 2020

(65) Prior Publication Data
US 2021/0220133 A1 Jul. 22, 2021

Related U.S. Application Data

(60) Provisional application No. 62/964,433, filed on Jan. 22, 2020.

(51) Int. Cl.
*A61F 2/24* (2006.01)
(52) U.S. Cl.
CPC ............ *A61F 2/2436* (2013.01); *A61F 2/243* (2013.01); *A61F 2220/0016* (2013.01)
(58) Field of Classification Search
CPC .............. A61F 2/2436; A61F 2/243; A61F 2220/0016; A61F 2/2442; A61F 2/2445; A61F 2/2418; A61F 2/2466; A61F 2/2409; A61B 2017/0649; A61B 2017/0647; A61B 17/064; A61B 2017/00243

See application file for complete search history.

(56) References Cited

U.S. PATENT DOCUMENTS

| | | | |
|---|---|---|---|
| 9,622,862 | B2 | 4/2017 | Lashinski et al. |
| 11,523,906 | B2* | 12/2022 | Inouye et al. |
| 2008/0262609 | A1 | 10/2008 | Gross et al. |
| 2011/0166649 | A1 | 7/2011 | Gross et al. |
| 2013/0123910 | A1 | 5/2013 | Cartledge et al. |
| 2013/0166017 | A1 | 6/2013 | Cartledge et al. |
| 2015/0112432 | A1 | 4/2015 | Reich et al. |
| 2017/0135816 | A1 | 5/2017 | Ashinski et al. |
| 2018/0228610 | A1* | 8/2018 | Lashinski ............. A61F 2/2466 |

OTHER PUBLICATIONS

International Search Report and Written Opinionfor the International Patent Application No. PCT/US2020/065576, dated Mar. 15, 2021, 32 pages.

* cited by examiner

Primary Examiner — Brooke Labranche
Assistant Examiner — Lauren Dubose
(74) Attorney, Agent, or Firm — Seager, Tufte & Wickhem LLP

(57) ABSTRACT

An implant includes a pair of anchors and a pair of anchor housing assemblies, wherein an anchor housing assembly includes an anchoring component configured to translate the anchor proximally-distally through the anchor housing assembly and a cinch component configured to control a space between the pair of anchor housing assemblies.

20 Claims, 13 Drawing Sheets

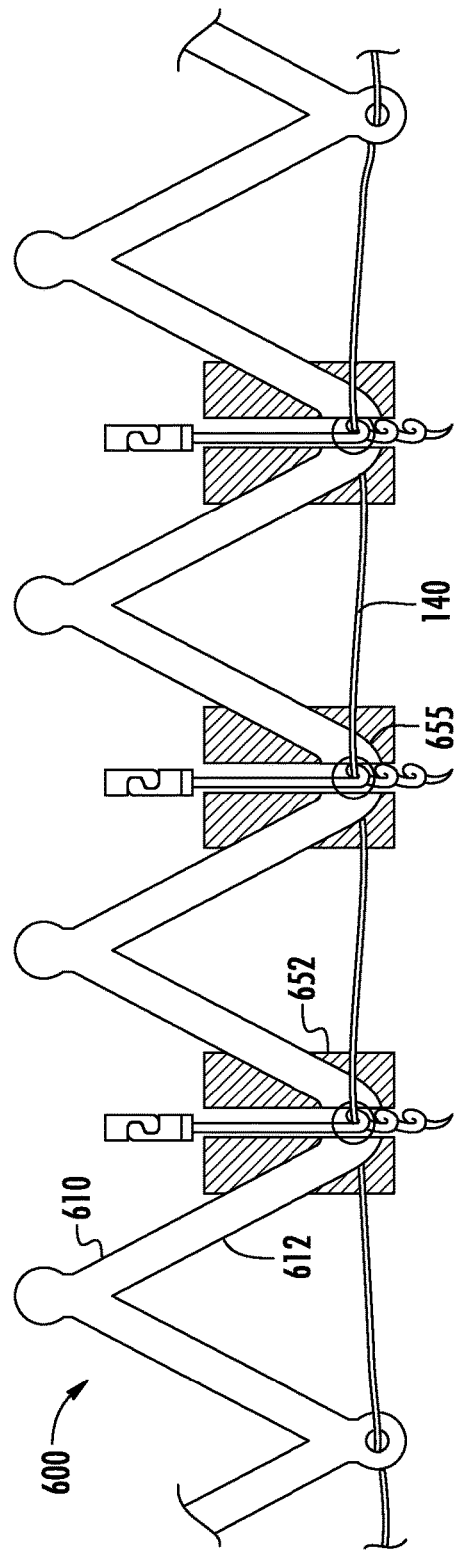
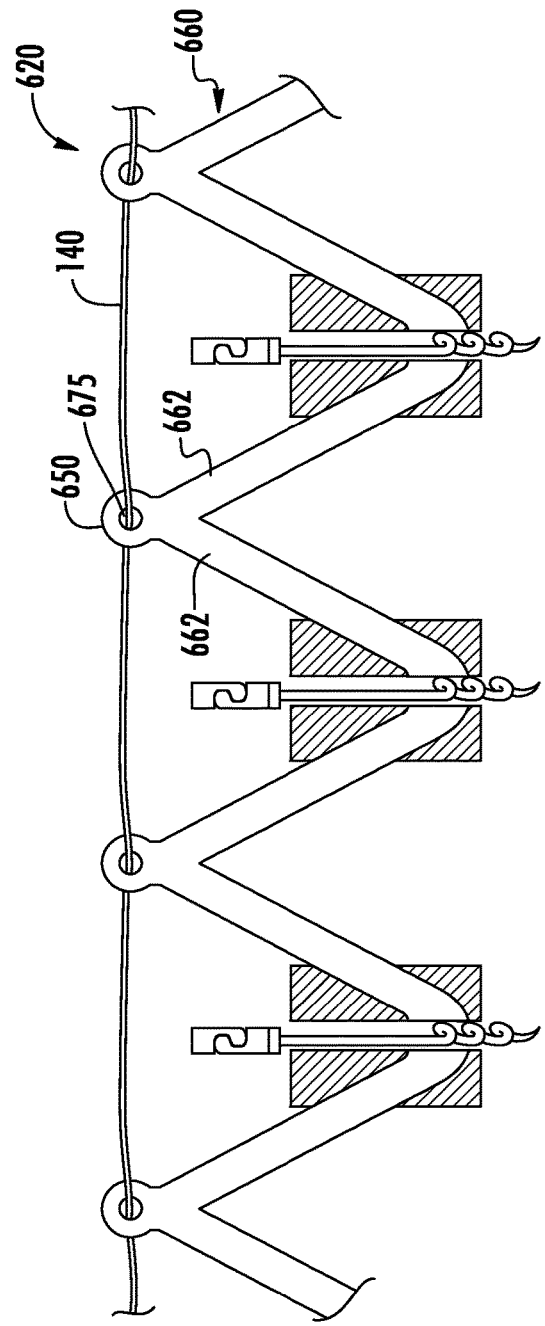
FIG. 6A
FIG. 6B

SIMPLIFIED COAXIAL SHAFT DESIGN DELIVERY SYSTEM AND IMPLANT FOR MITRAL VALVE ANNULUS REDUCTION

CROSS-REFERENCE TO RELATED APPLICATIONS

The present application claims the benefit of priority under 35 U.S.C. § 119 to U.S. Provisional Patent Application 62/964,433, filed Jan. 22, 2020, which application is incorporated herein by reference in its entirety for all purposes.

FIELD

The present disclosure relates generally to the field of implantable medical devices. In particular, the present disclosure relates to medical devices, systems, and methods for annuloplasty and other cardiac treatment techniques.

BACKGROUND

Mitral insufficiency (MI) (also referred to as mitral regurgitation or mitral incompetence) is a form of heart disease where the mitral annulus dilates excessively and the valve leaflets no longer effectively close, or coapt, during systolic contraction. Regurgitation of blood occurs during ventricular contraction and cardiac output may decrease as a result. Surgical and endoluminal annuloplasty techniques have been introduced that aim to restore a mitral valve to its native configuration, for example by implanting an annuloplasty ring around a valve annulus. One problem encountered by such implants is that their size may cause unintended contact between the implant and the cardiac wall, reducing the efficacy of the implant. It is desirable to minimize the size of an implant to reduce the opportunity for such contact and it is with these considerations in mind that the improvements of the present disclosure may be useful.

SUMMARY

Embodiments of the present disclosure relate to a valve reshaping implant that incorporates both cinching and anchoring components into an anchor housing assembly. In one embodiment, the cinching and anchoring components may be configured for independent control by a pair of coaxially disposed drivers, thereby advantageously reducing delivery catheter profile.

According to one aspect, an implant includes a pair of anchors, where an anchor of the pair of anchors includes a proximal drive coupler and a distal helical anchor portion. The implant includes a pair of anchor housing assemblies, where an anchor housing assembly of the pair of anchor housing assemblies includes an anchoring component configured to translate the anchor along a first axis parallel to a central axis extending proximally-distally through the anchor housing assembly and a cinch component configured to control a space between the pair of anchor housing assemblies.

In one embodiment, the anchor housing assembly may include a body having a bore extending along the first axis therethrough. The bore includes a bore circumference defined by an inner surface and the inner surface of the bore may include a threaded portion configured to axially translate the anchor along the first axis through the bore when a first driving force is applied to the proximal drive coupler of the anchor. In one embodiment, the implant may include a frame having a plurality of struts, a first pair of struts joined (such as at proximal ends) at a proximal apex, a second pair of struts joined (such as at distal ends) at a distal apex, and where the anchor housing assembly is coupled to the frame about the distal apex. In some embodiments, the frame may be releasably coupled to the anchor housing assembly. In one embodiment, the cinch component includes a threaded shaft extending proximally from the anchor housing and a collar disposed about the distal apex of the frame and the threaded shaft, the collar configured to axially translate along the threaded shaft and the distal apex in response to rotation of the threaded shaft about the first axis, to modify a strut spacing between the second pair of struts of the distal apex. In one embodiment, the threaded shaft includes a shaft bore extending therethrough and the shaft bore is axially aligned with the bore of the anchor housing. A shaft bore circumference may exceed an external diameter of an anchor drive shaft. The collar may include a first frame sleeve, and the second pair of struts of the distal apex may be translatably disposed within the collar. The anchor housing assembly may include a pair of frame sleeves, and one strut of the second pair of struts may be translatably disposed in a first sleeve of the pair of frame sleeves and another strut of the second pair of struts may be translatably disposed within a second sleeve of the pair of frame sleeves.

In one embodiment, a distal end of the threaded shaft includes a flange that extends radially from an external surface of the threaded shaft, and the body of the anchor housing assembly may include a retention feature, such as a slot and corresponding arm or finger (hereinafter "slot" for the sake of convenience without intent to limit), configured to retain the flange of the threaded shaft to secure the threaded shaft to the anchor housing. The cinch component may include a tether and a tether guide, and the tether guide may include a tether lumen extending through the proximal apex of the frame or through the distal apex of the frame, wherein the tether is slidably disposed within the tether lumen to control the space between the pair of anchor housing assemblies.

In one embodiment, the tether guide of the cinch component includes a spool, the tether is coupled to the spool and the spool is configured to rotate about a second axis parallel to the central axis to wind or to unwind the tether from the spool to control the space between a pair of anchor housing assemblies.

According to another aspect, an implant delivery system includes an implant and a pair of anchors, where an anchor of the pair of anchors includes a proximal drive coupler and a distal helical anchor portion, and a pair of anchor housing assemblies. An anchor housing assembly includes an anchoring component configured to translate the anchor along a first axis parallel to a central axis extending proximally-distally through the anchor housing assembly, and a cinch component coupling the pair of anchor housing assemblies. The implant delivery system includes a delivery catheter including a cinch driver releasably coupled to the cinch component of the anchor housing assembly. The cinch driver may be operable, when actuated, to cause the cinch component to control a space between the pair of anchor housing assemblies. The cinch driver may have a cinch driver lumen extending therethrough, the cinch driver lumen coaxial with the first axis. The delivery catheter may also include an anchor driver releasably coupled to the anchoring component of the anchor housing assembly, the anchor driver disposed within the cinch driver lumen.

In various embodiments, the system may include an alignment mechanism configured to maintain coaxial alignment between the cinch component and the anchoring component of the anchor housing assembly, the alignment mechanism including a sheath, a pin, or a combination thereof. In some embodiments, the implant further includes a frame having a plurality of struts, a first pair of struts joined (such as at proximal ends) at a proximal apex, a second pair of struts joined (such as at distal ends) at a distal apex, and where the anchor housing assembly is coupled to the frame about the distal apex.

In some embodiments, the cinch component of the anchor housing assembly further includes a collar configured to translate axially along the second pair of struts to control the space between the pair of anchor housing assemblies. In some embodiments, the cinch component of the anchor housing assembly further includes a tether and a tether guide. In some embodiments, the tether guide includes a tether lumen extending through the distal apex of the frame, or a rotatable spool, or both.

According to a further aspect, a method of delivering an implant to a valve treatment site includes the steps of advancing the implant to a treatment site. In some embodiments, the implant includes a tubular frame comprised of a plurality of sinusoidally joined struts including first pairs of struts joined at proximal apices, and second pairs of struts joined at distal apices. The implant may also include a pair of anchor housing assemblies, a first anchor housing assembly of the pair of anchor housing assemblies coupled to a first distal apex of the tubular frame, a second anchor housing assembly of the pair of anchor housing assemblies coupled to a second distal apex of the tubular frame. The second anchor housing assembly may include a body including an anchoring component and a cinching component, a bore extending along a central bore axis disposed proximally-distally through the body of the first anchor housing assembly, and an anchor translationally disposed within the bore. The method may include positioning the tubular frame about the valve treatment site and actuating an anchor drive shaft, coupled to the anchoring component of the first anchor housing assembly, to translate the anchor through the bore along the central bore axis into the valve treatment site. The method of delivering also includes controlling a spacing between anchor housing assemblies using a cinch drive tube that is coaxially disposed about the anchor drive shaft. In various embodiments, the method may include releasing the tubular frame from the anchor housing assemblies and withdrawing the tubular frame from the valve treatment site.

With such an arrangement, a low-profile implant having a reduced delivery cross-section profile provides a less-invasive valve restructuring solution.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical illustrated component is typically represented by a single numeral. For purposes of clarity, not every component is labeled in every figure, nor is every component of each embodiment shown where illustration is not necessary to allow those of ordinary skill in the art to understand the disclosure. In the figures:

FIGS. 6A and 6B illustrate embodiments of implants comprising tethers and co-axial cinching and anchoring components as disclosed in various embodiments herein;

DETAILED DESCRIPTION

An implant as disclosed herein integrates cinching and anchoring components within an anchor housing assembly, wherein the cinching and anchoring components may be coaxially arranged for independent control using coaxially nested drivers. Integrating anchoring and cinching functionality in this manner reduces by half the number of drive tubes used to independently control anchoring and cinching for the implant, thereby allowing customization of implant restructuring with a less invasive, reduced cross section catheter.

As described in more detail below, in one embodiment the cinching component may include a tether coupling the anchor housing assemblies, and mechanisms for reducing a circumference formed by the tether. In one embodiment, the cinching mechanism may include a collar disposed for translation along a pair of struts of a distal apex of a frame of the implant. The collar may include one or more sleeves disposed about a threaded shaft and one or more of the struts of the pair, wherein proximal advancement of the collar over the one or more struts of the pair reduces a spacing between the pair of struts.

These and other beneficial aspects of an implant and method of deployment are described in more detail below. Although embodiments of the present disclosure may be described with specific reference to mitral valves, the principles disclosed herein may be readily adapted to facilitate reconstruction of any valve annulus, for example including a tricuspid valve annulus and/or may similarly benefit any other dilatation, valve incompetency, valve leakage, and other similar heart failure conditions.

In addition, although a transseptal delivery may be described, it is appreciated that the implant may be delivered in a minimally invasive percutaneous manner, such as transfemorally, transseptally, or transapically. In addition, the implant may be implanted surgically, in that it should reduce the duration of the procedure and, more particularly, the duration that the patient is on bypass.

As used herein, the term "distal" refers to the end farthest away from the medical professional when introducing a medical device into a patient, while the term "proximal" refers to the end closest to the medical professional when introducing a medical device into a patient.

Figure 1:
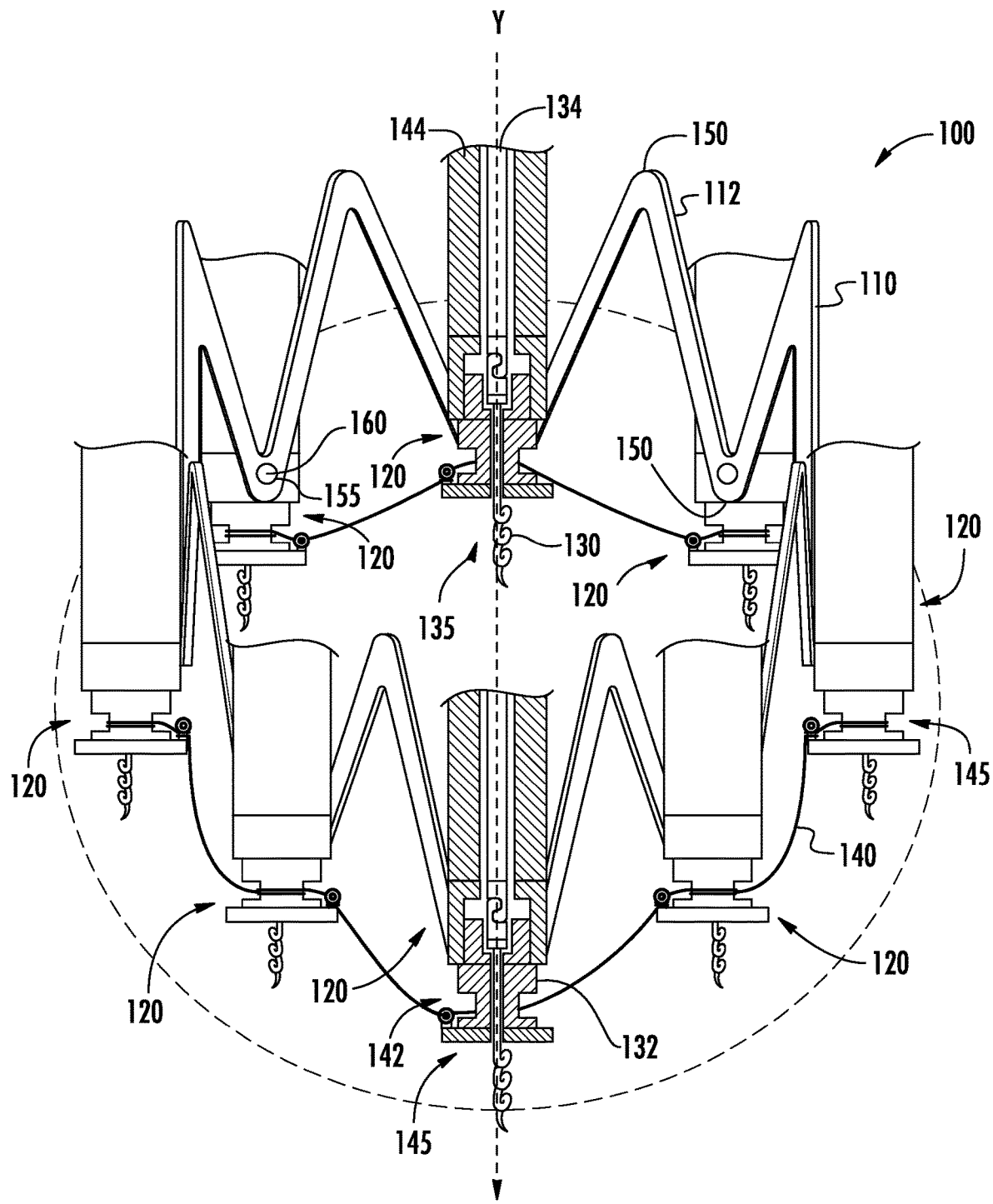
FIG. 1 is a diagram of one embodiment of an implant comprising co-axial cinching and anchoring components as disclosed in various embodiments herein.

FIG. 1 illustrates an implant 100 comprising a frame 110 that may be disposed about a heart valve annulus 111 or other cardiac feature. For purposes of clarity not all of the components of the implant are numbered. In one embodiment, the frame 110 may extend circumferentially around and partially axially along a central frame axis Y extending proximally-distally through a center point of the frame 110. The frame 110 may be generally symmetrical with respect to the central frame axis although it need not be symmetrical (e.g., D-shaped, oval, etc.). The frame 110 may form a generally tubular shape, where herein "tubular" includes circular as well as other rounded or otherwise closed shapes. The frame 110 may be configured to change shape, size, and/or configuration. For example, the frame 110 may assume various shapes, sizes, configurations etc. during different phases of deployment such as during pre-delivery, delivery, tissue engagement, and cinching.

According to one embodiment, the frame 110 may be formed from one or more struts 112 that may form all or part of the frame 110, where the struts 112 may include elongated structural members formed of a metal alloy, a shape memory material (such as an alloy of nickel titanium or other metals), plastics, polymers, composites, other suitable materials, or combinations thereof. In FIG. 1 sixteen struts 112 are shown (not each individually labeled) although it is appreciated that in some embodiments, there may be fewer or more than sixteen struts.

In one embodiment, the struts 112 of the frame 110 may be formed from the same, monolithic piece of material (e.g., tube stock). Thus, reference to struts 112 may refer to different portions of the same, extensive component. Alternatively, reference to struts 112 may refer to components that are formed separately and attached permanently together, for example by welding or other methods. In some embodiments, the struts 112 may be separate components that are detachably coupled to form proximal apices 150 and distal apices 152. For instance, the struts 112 may be coupled at proximal ends thereof to form the proximal apices. Additionally, or alternatively, the struts 112 may be coupled at distal ends thereof to form the distal apices 152.

In some embodiments, the terms "apex," apices," and the like may be used interchangeably with terms "crown," "crowns," and the like, as used herein and as used in any reference incorporated by reference herein, unless otherwise stated. In one embodiment, an "apex" may include a proximal or distal portion of the frame.

The implant further includes anchor housing assemblies 120 coupled by a tether 140. The anchor housing assemblies 120 may include anchoring components 135, configured to attach the anchor housing assemblies 120 to tissue, and cinching components 145 configured to draw anchor housings 120 together to reshape the valve annulus.

The anchor housing assemblies 120 may be coupled to the distal apices 152 of the frame 110. In some embodiments the anchor housings 120 may be releasably coupled to the frame 110. For example, in the embodiment of FIG. 1, the frame 110 is shown to include an opening 155 at the distal apex. A boss 160, extending radially inward from the anchor housing assembly 120 towards the central axis Y of the frame may be press fit through the opening 155 at the distal apex 152. The frame 110 may include a biased configuration that expands radially outward from the central axis Y, wherein the expansion force of the biased configuration retains the boss 160 within the hole 155. In other embodiments, as described in more detail below, the anchor housing assemblies 120 may include sleeves, collars, or other mechanisms for coupling the anchor housing assemblies 120 to the frame 110.

Anchoring components 135 are shown to include anchor 130, anchor housing body 132, and anchor drive shaft 134. Actuation of the anchor drive shaft 134 (i.e., rotation of the tube), translates the anchor 130 through the anchor housing body 132 and into tissue of the annulus 111.

Cinching components 145 are shown to include a rotatable spool 142 and a cinch drive tube 144, wherein the anchor drive shaft 134 is coaxially nested within cinch drive tube 144. In one embodiment, the rotatable spool 142 provides a tether guide, wherein rotation of the rotatable spool operates to wind and to unwind the tether 140 from the spool to pull together anchor housing assemblies 120.

Figure 2A:
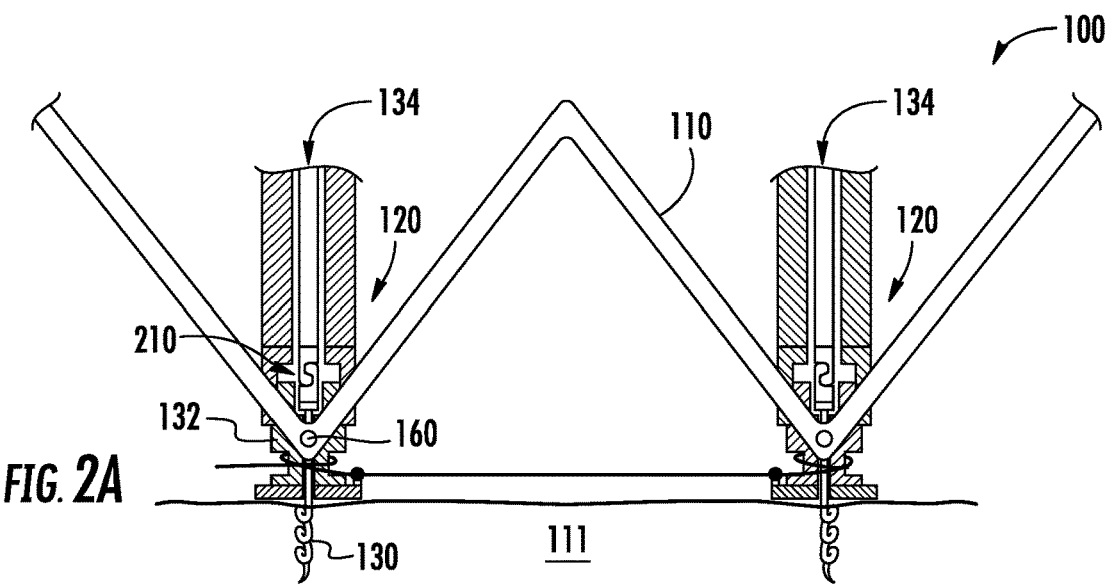
FIGS. 2A-2C illustrate a portion of the implant of FIG. 1 for describing one method of cinching and anchoring an implant as disclosed herein.

FIG. 2A is a perspective view of a portion of an implant 100 including two anchor housing assemblies 120 facing radially inward to the central axis Y (see FIG. 1) of the frame 110 and coupled to the frame 110 via bosses 160. The implant 100 is shown in an anchored configuration, wherein anchors 130 have been driven through a bore 210 of anchor housing body 132 of the anchor housing assembly 120 and into tissue of the annulus 111, for example by rotation of anchor drive shaft 134.

Figure 2B:
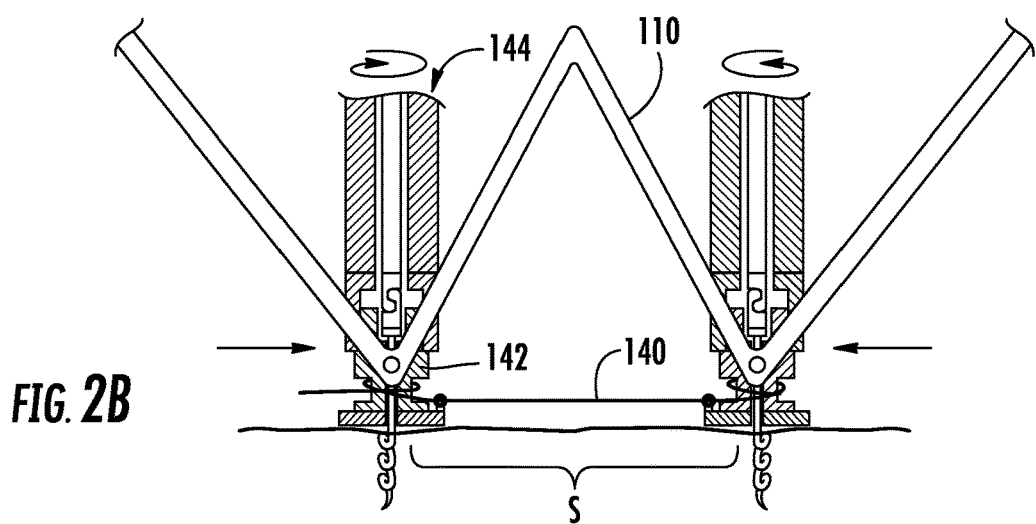

Following anchoring, as shown in FIG. 2B, actuation of the cinch drive tube 144 rotates the spool 142, winding the tether 140 around the spool 142 and reducing a space S between the anchor housings 120. In one embodiment, the spool 142 may include a groove which guides and/or couples the tether to and/or around the spool 142. In some embodiments, the spool 142 may include a ratchet type winding mechanism, allowing rotation, or winding, of the of the spool in one direction and inhibiting rotation, or unwinding of the spool in a second, opposite direction. With such an arrangement, a custom valve reshaping solution that enables independent customization of anchor housing assembly spacing may be provided.

Figure 2C:
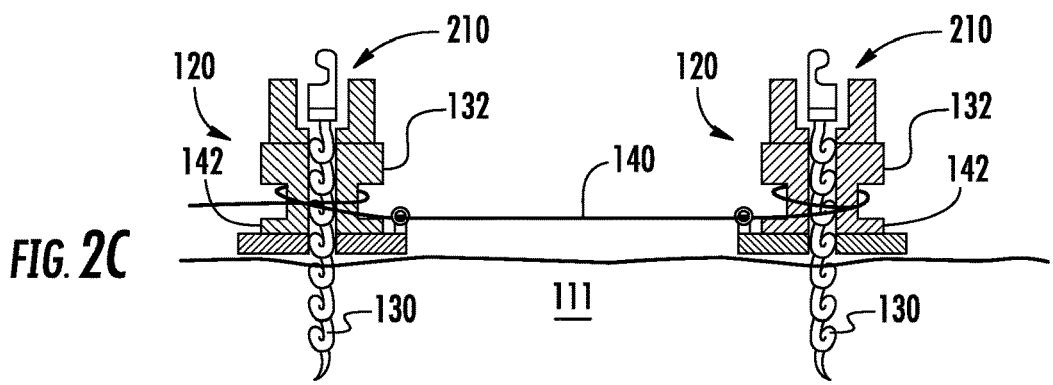

FIG. 2C illustrates a resulting portion of a low-profile implant 100, following cinching as shown in FIG. 2B and removal of the frame and drivers from the annulus 111. The anchors 130 remain driven through the bore 210 of the anchor housing body 132 and the spools 142 and tether 140 retain the custom annulus reshaping.

Figure 3A:
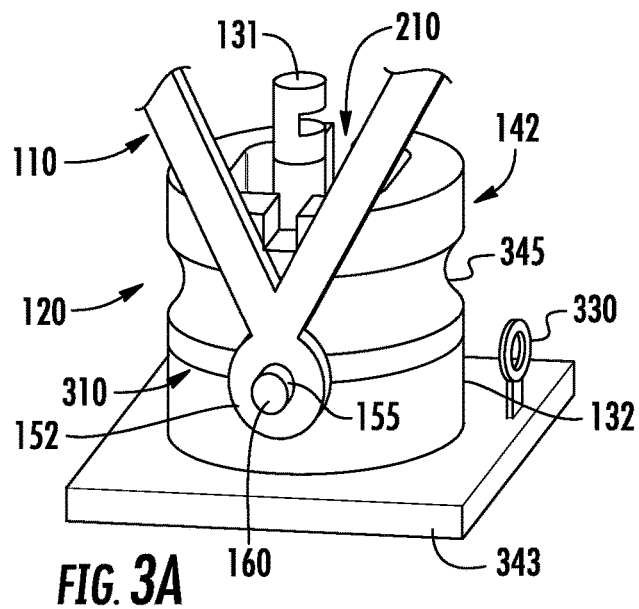
FIGS. 3A-3C illustrate perspective views of one embodiment of an anchor housing assembly comprising coaxial cinching and anchoring components.
Figure 3B:
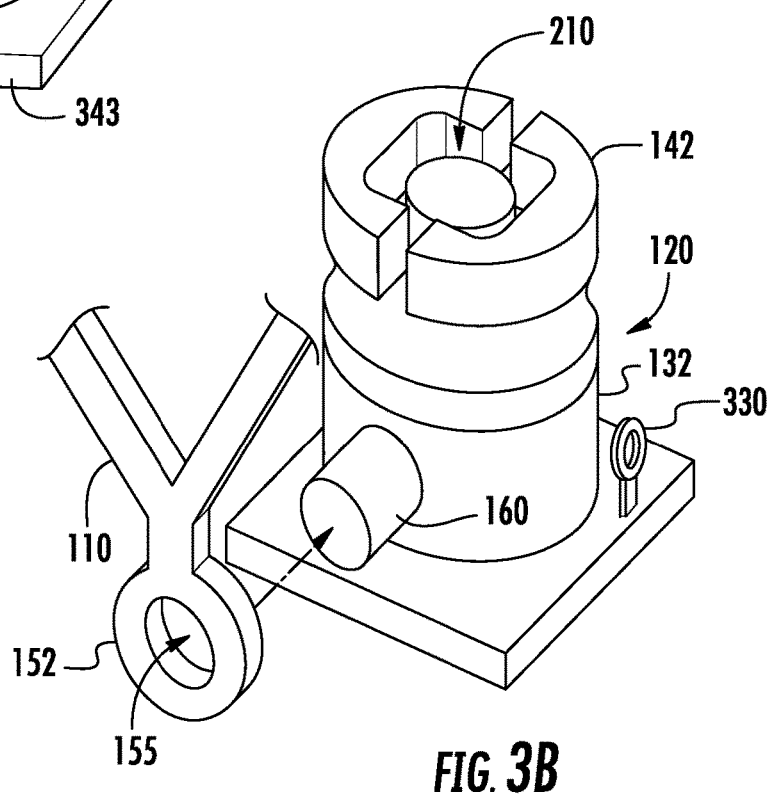
Figure 3C:
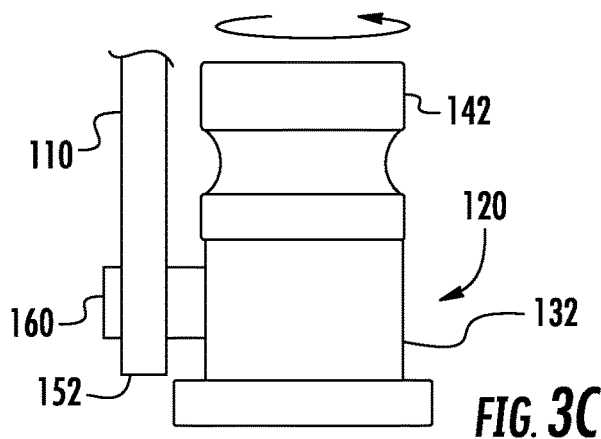

FIGS. 3A-3C provide close up perspective views of one embodiment of an anchor housing assembly 120, and a distal apex 152 of a frame 110. In FIG. 3A the spool 142 can be seen rotatably disposed upon anchor housing body 132. The spool 142 and anchor housing body 132 may have ridged or cleated opposing surfaces 310, forming a ratchet type connection that enables the spool 142 to rotate freely over the anchor housing body 132 in a first rotation direction, but inhibits free rotation over the anchor housing body 132 in a second, opposing rotation direction.

A proximal coupler 131 of the anchor is shown advanced within the bore 210 of the anchor housing assembly 120. The boss 160 can be seen extending through the opening 155 of the distal end 152 of the frame 110. In some embodiments, the anchor housing body 132 may be disposed on or integral with a base 343 (illustrated shape being illustrative, but not limiting), which may support an eyelet 330. In some embodiments, the eyelet 330 may, together with the curved portion 345 of the spool 142, form a tether guide for guiding the tether between anchor housings assemblies 120 and around the spool 142.

FIG. 3B illustrates the anchor housing assembly 120 with the anchor removed, wherein the bore 210 may be seen to extend through the spool 142 and the anchor housing body 132. The frame 110 is shown being press fit or removed from the anchor housing assembly 120, for example, by inserting or removing the boss 160 from the opening 155 in the distal apex 152 of the frame 110. FIG. 3C is a side perspective view of the anchor housing assembly 120, following press fitting of opening 155 (at the distal end 152 of the frame 110) over the boss 160. The boss extends radially inward, in one embodiment, for a distance sufficient to separate the frame 110 from the spool 142, to allow for free rotation of the spool 142 during cinching.

Figure 4A:
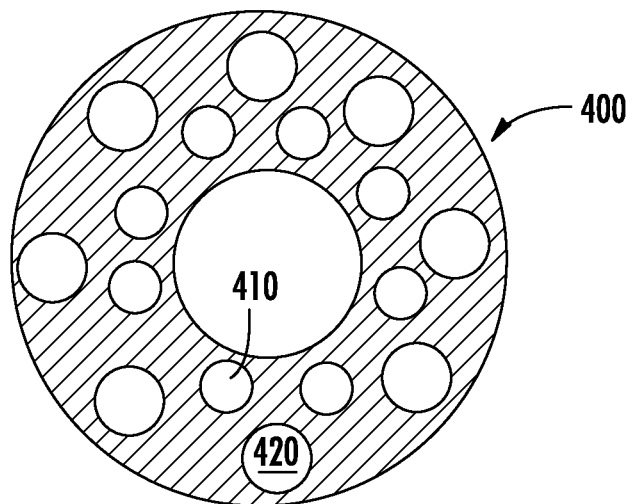
FIGS. 4A and 4B are, respectively, views of a prior art delivery catheter cross-section and a cross-section of one embodiment of an implant delivery catheter as disclosed herein.

One advantage of integrating anchoring components and cinching components in a manner that enables coaxial, independent driving of the individual components is that full customization can be delivered with a reduced profile delivery catheter. For example, FIG. 4A is a cross section view of one embodiment of a prior art delivery catheter 400 configured to include eight anchor driver lumens 410 and eight cinch driver lumens 420 resulting in a catheter 400 comprising an outer diameter (OD) around 24 Fr and upwards of about 36 Fr. It will be appreciated that fewer (e.g., as few as four) or more (e.g., as many as twelve) anchor driver lumens and cinch driver lumens may be used without departing from the spirit of the present disclosure.

Figure 4B:
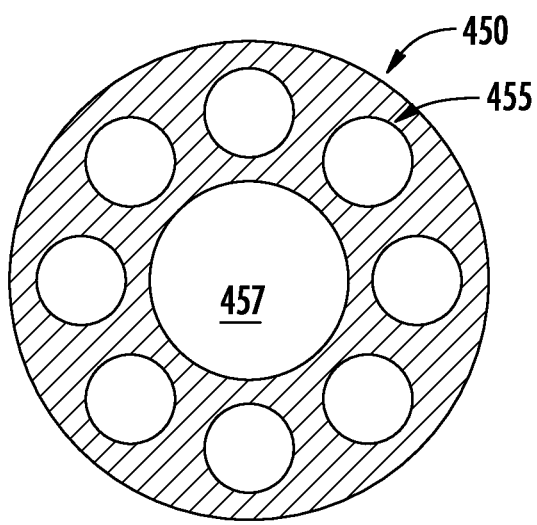

In contrast, FIG. 4B illustrates a cross section of one embodiment of a delivery catheter 450 that may be used to deliver implants configured as disclosed herein to include a plurality of coaxial driver lumens 455. In one embodiment, the delivery catheter 450 may comprise a composite of layers of thermoplastic elastomer (TPE), for example PEBAX provided by ARKEMA corporation of Colombes, France. Alternatively, nylon, polyurethanes, polyester, silicone, or other similar materials may be used to provide thin walls that may be extruded and layered over braided wires or coils for tensile and hoop strength, although the disclosed system is not limited to any particular material composition for the delivery catheter. In some embodiments, the length of the delivery catheter 450 may range from between 24"-52", and more particularly between 42"-46", enabling transseptal, transapical, and/or transfemoral delivery of the implant. In one embodiment, an inner, working channel 457 diameter may be, for example, approximately 12 Fr and the outer diameter may be 28 Fr. A cross section diameter of the anchor cinching lumens 455 may be, for example at least about 0.5 mm and at most about 3 mm, for example 2 mm, although the present invention is not so limited.

Figure 5A:
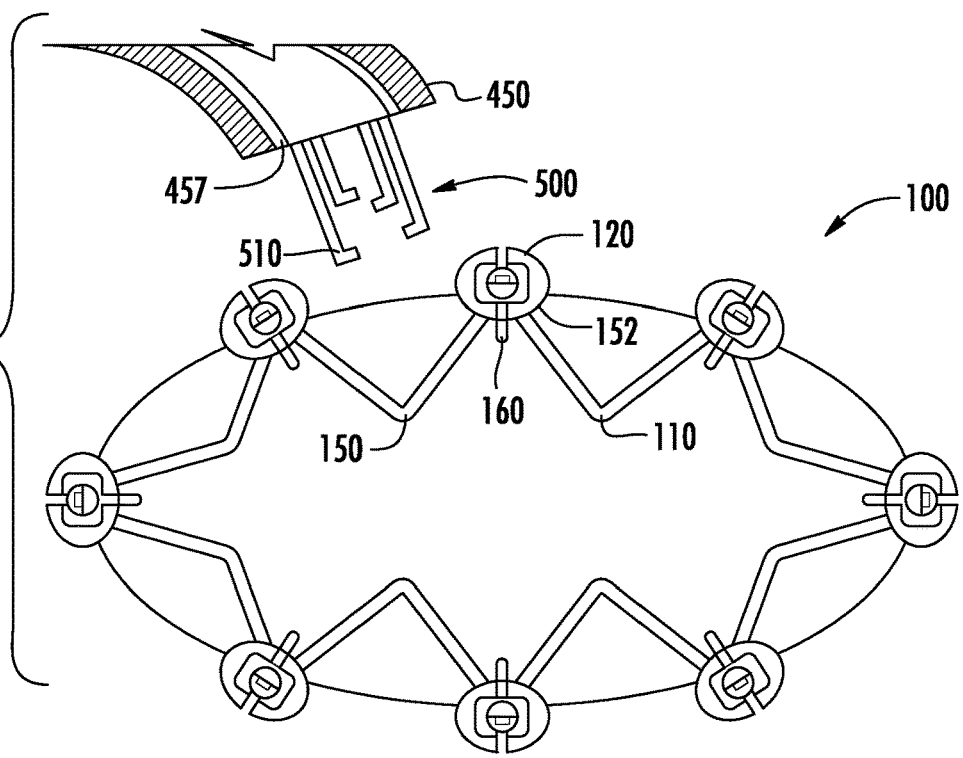
FIGS. 5A and 5B are perspective views of one embodiment of an implant following cinching and anchoring and illustrating an example of a method and tool for implant frame removal.

In one embodiment, the working channel 457 may be used to advance implant delivery tools to the annulus. For example, referring now to FIG. 5A, a top down view of implant 100 is shown comprising a plurality of anchor housing assemblies 120 following deployment and cinching, but prior to removal of the frame 110. A frame retrieval tool 500 may be advanced through the working channel 457 of delivery catheter 450. The retrieval tool 500 may include hooks 510, loops, or other mechanisms (e.g., interlocking configurations, ball and socket mating components, latches, etc.) or properties (such as magnetism) for engaging with a proximal end 150 of the frame 110, to release the opening in the distal end 152 of the frame 110 from the boss 160.

Figure 5B:
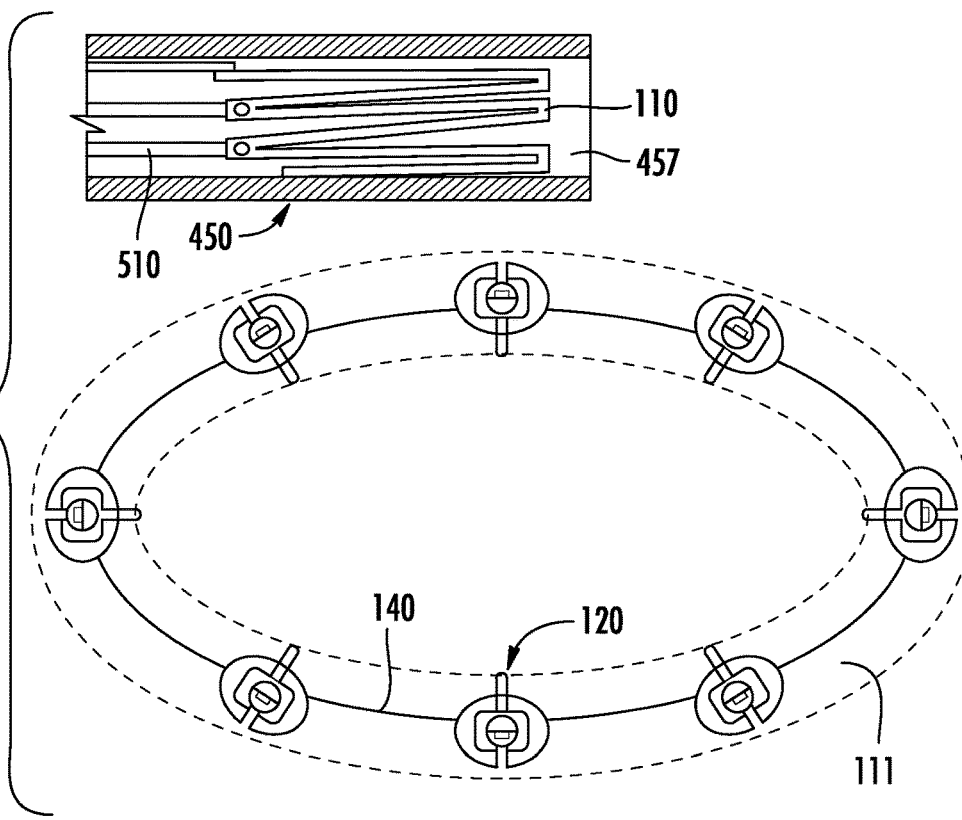

FIG. 5B illustrates the delivery catheter 450, following withdrawal of the frame 110 into the working channel 457 of the catheter 450 by action of the hooks 510. The resulting low-profile implant 100, including anchor housing assemblies 120 and tether 140, remains to retrain the annulus 111 in a reshaped configuration.

FIG. 6A illustrates a portion of an alternate embodiment of an implant 600, wherein the implant 600 comprises a frame 610 comprised of struts 612 joined at distal ends as distal apices 652. A tether guide of implant 600 includes a tether lumen 655 extending through the distal apices 652 of the frame 610 and sized to allow the tether 140 to be advanced through the tether lumens 655 around the frame 610 to reduce the circumference of the frame.

FIG. 6B illustrates a portion of an alternate embodiment of an implant 620, wherein the implant 620 comprises a frame 660 comprised of struts 662 joined at proximal apices 650. For instance, struts 662 may be joined at proximal ends thereof to form proximal apices 650. A tether guide of implant 620 includes a tether lumen 675 extending through the proximal apices 650 of the frame 660 and sized to allow the tether 140 to be advanced through the tether lumens 675 around the frame 660 to reduce the circumference of the frame 660.

Figure 7:
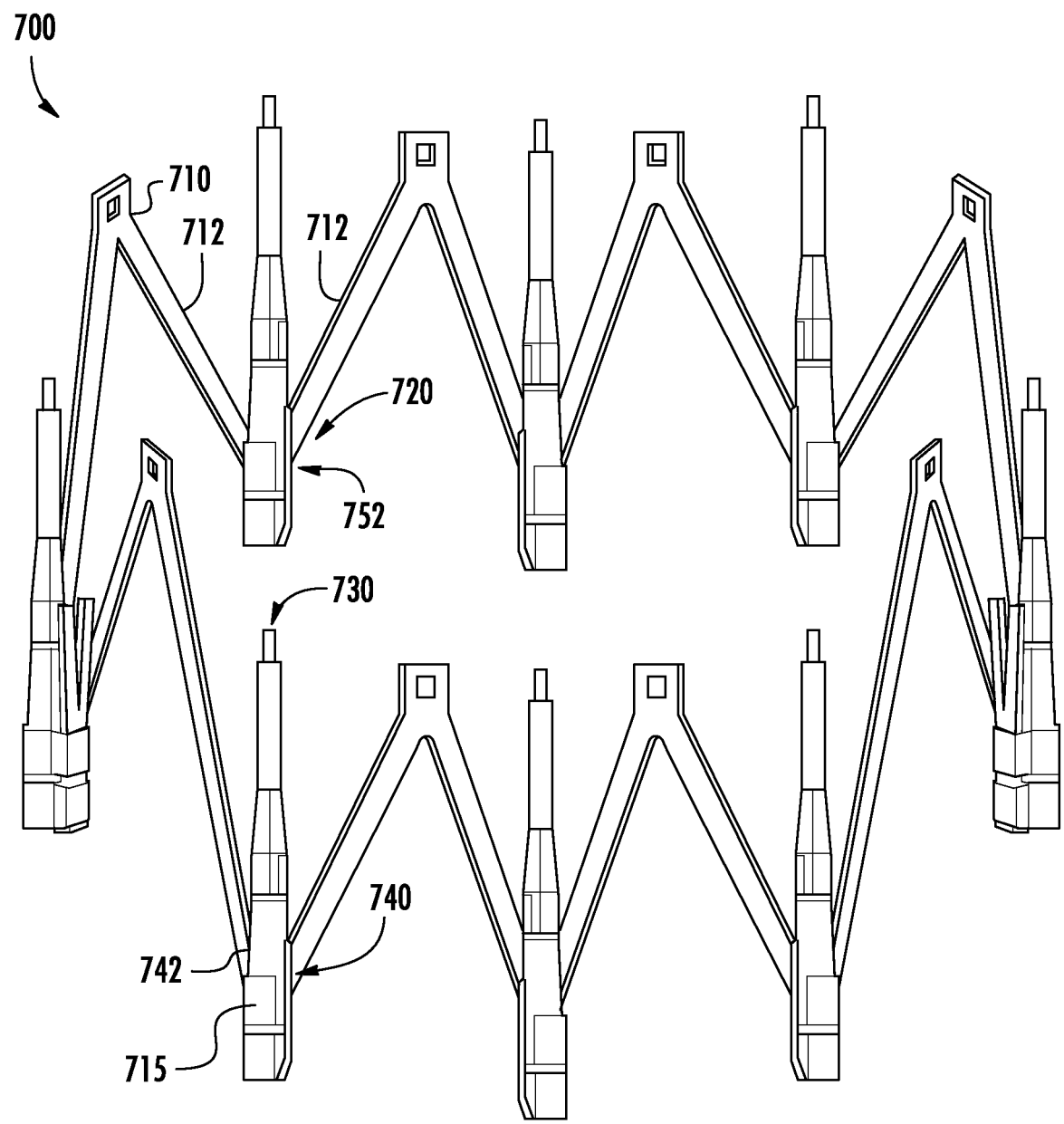
FIG. 7 illustrates an embodiment of an implant comprising a collar based co-axial cinching component as disclosed in various embodiments herein.

FIG. 7 illustrates an alternate embodiment of an implant 700 comprising a frame 710 comprising a plurality of struts 712 coupled at distal apices 752 to anchor housing assemblies 720. According to one embodiment, the anchor housing assemblies 720 include an anchoring component 730 and a cinch component 740. The cinch component 740 is comprised of a threaded shaft 742 and a translatable or dynamic sliding cinch sleeve or distal collar (hereinafter "distal collar" for the sake of convenience without intent to limit) 715.

Figure 8:
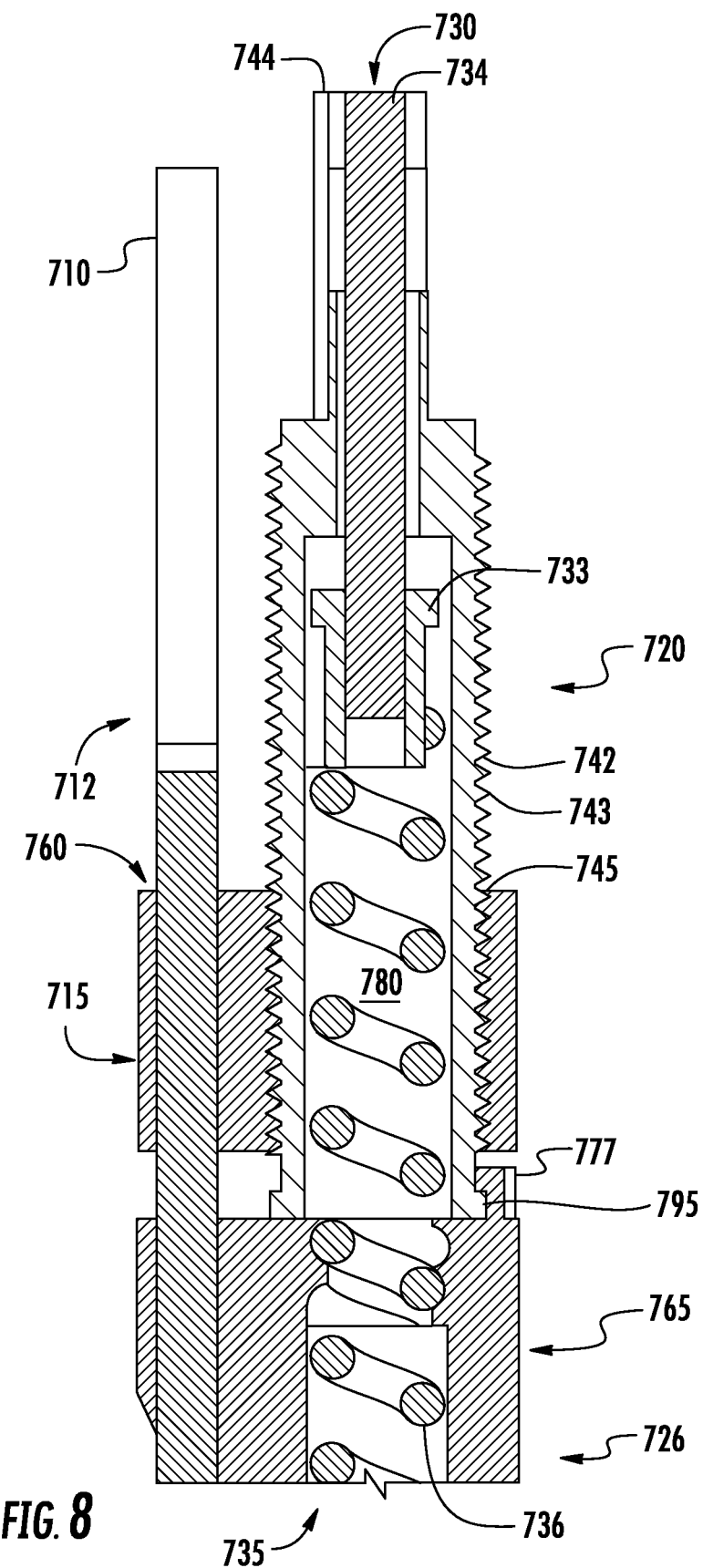
FIG. 8 is a cross-section diagram of one embodiment of a collar based co-axial cinching component as disclosed herein.

FIG. 8 is a cross-sectional view of one embodiment of the anchor housing assembly 720. The anchor components 730 of the anchor housing assembly 720 include an anchor drive shaft 734, and an anchor 735, wherein the anchor 735 comprises a proximal coupler 733 and a distal helical portion 736. In one embodiment, the proximal coupler 733 is configured for mated engagement with the anchor drive shaft 734, such that rotation of the anchor drive shaft 734 rotates the anchor 735.

In one embodiment, the threaded shaft 742 of the cinch component 740 includes an external threaded surface 743 and a bore 780 extending therethrough. The distal collar 715 is disposed about the threaded shaft 742, wherein the distal collar 715 includes an internal bore 745 having internal surface engagement features, such as grooves or complimentary threads, that are configured to interact with external features 743 of the threaded shaft 742 such that rotation of the threaded shaft 742 by a cinch drive tube 744 axially translates the collar 715 over the threaded shaft 742.

In one embodiment, a distal end 726 of the anchor housing assembly 720 includes an anchor housing body 765. In one embodiment, the anchor housing body 765 is shaped and configured (such as by provision of a slot 777, described in further detail below) to cooperate with a flange 795 at the distal end of the threaded shaft 742 to matingly engage the threaded shaft 742 with the anchor housing body 765.

In one embodiment, the collar 715 includes a sleeve 760. The sleeve 760 at least partially surrounds the struts 712 of the frame, such that proximal translation of the distal collar 715 over the struts 712 of the frame 710 changes the spacing between the struts 712 and pulls together anchor housing assemblies 720.

Figure 9A:
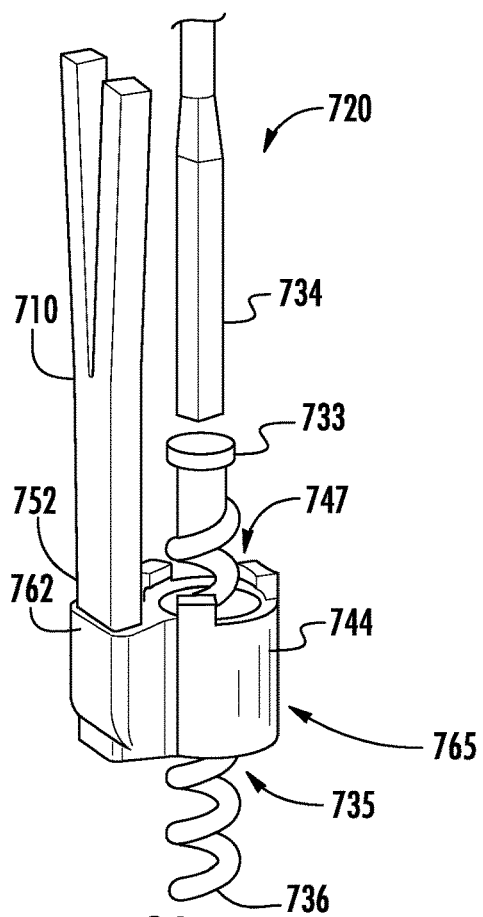
FIGS. 9A-9D illustrate examples of components of one embodiment of a collar based co-axial cinching component as disclosed herein.

FIGS. 9A-9D illustrate various components of an anchor housing assembly 720 in more detail. FIG. 9A illustrates the anchor housing body 765, having a distal anchor bore 747 extending therethrough. The distal helical portion 736 of the anchor 735 translates through the bore 747 of the cinch drive tube 744 by interaction of the anchor drive shaft 734 and the proximal coupler 733. The sleeve 762 is shown with the distal apex 752 of the frame 710 extending therethrough.

Figure 9B:
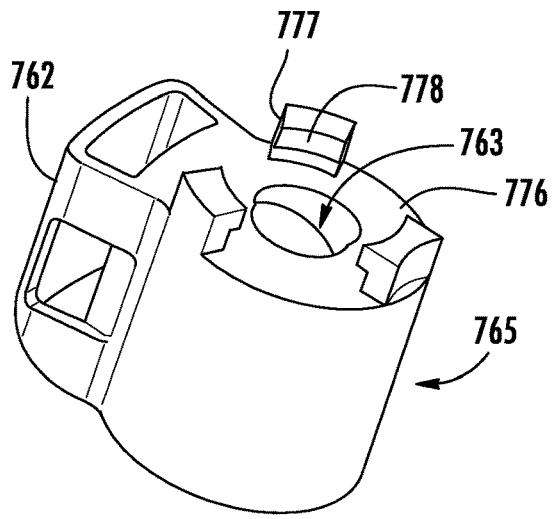

FIG. 9B is a perspective view of an anchor housing body 765. The frame sleeve 762 is configured to slidably accept a distal apex 752 of the frame 710, and the anchor housing body 765 includes an internal bore 763 that extends proximally-distally along an axis through the anchor housing body 765. In one embodiment, a proximal surface 776 of the anchor housing body 765 is shaped and configured to engage with the threaded shaft 742 as previously described to couple the threaded shaft 742 to the anchor housing assembly 720. For example, one or more slots 777, such as formed by one or more radially inwardly extending fingers or arms 778, may be provided at the proximal surface 776 of the anchor body housing 765 to receive or mate with the flange 795 at the distal end of the threaded shaft 742.

Figure 9C:
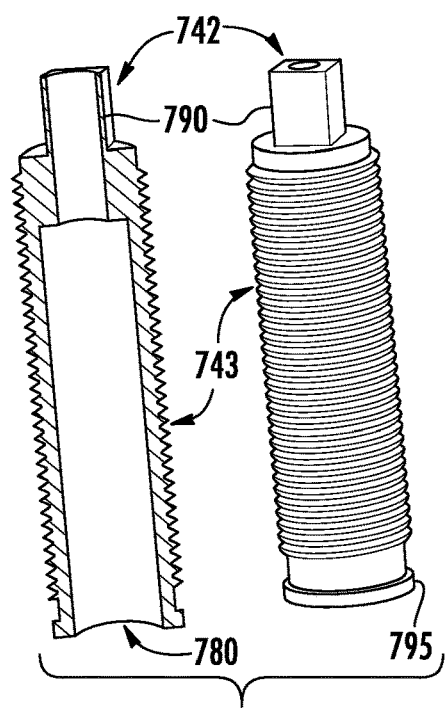

FIG. 9C is a cross-sectional and perspective view of the threaded shaft 742, which includes an internal bore 780 sized to accommodate the anchor 736 and the anchor drive shaft 734. In one embodiment, the threaded shaft 742 includes an external threaded portion 743 that extends at least partially longitudinally along an exterior surface of the threaded shaft 742. The threaded shaft may also comprise, at its proximal end, a cinch drive coupler 790, configured to couple with a cinch drive tube 744. The cinch drive coupler 790 is configured to enable coaxial advancement of the anchor drive shaft 734 though the bore 780 of the threaded shaft 742. A distal end of the threaded shaft 742 may include a flange 795, extending radially from an external surface 743 of the threaded shaft 742 and configured to interact with the anchor housing body 765 (such as described above) to secure the threaded shaft 742 to the anchor housing assembly 720.

Figure 9D:
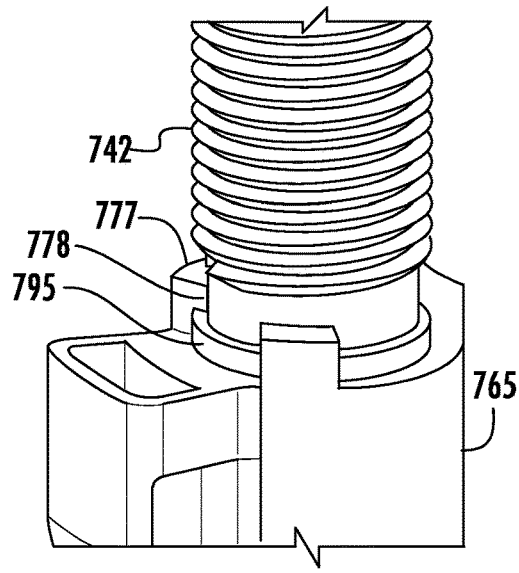

FIG. 9D illustrates the threaded shaft 742 secured to the anchor housing body 765 wherein the flange 795 is disposed within a slot 777 formed by an arm or finger 778 of the anchor housing body 765.

Figure 10A:
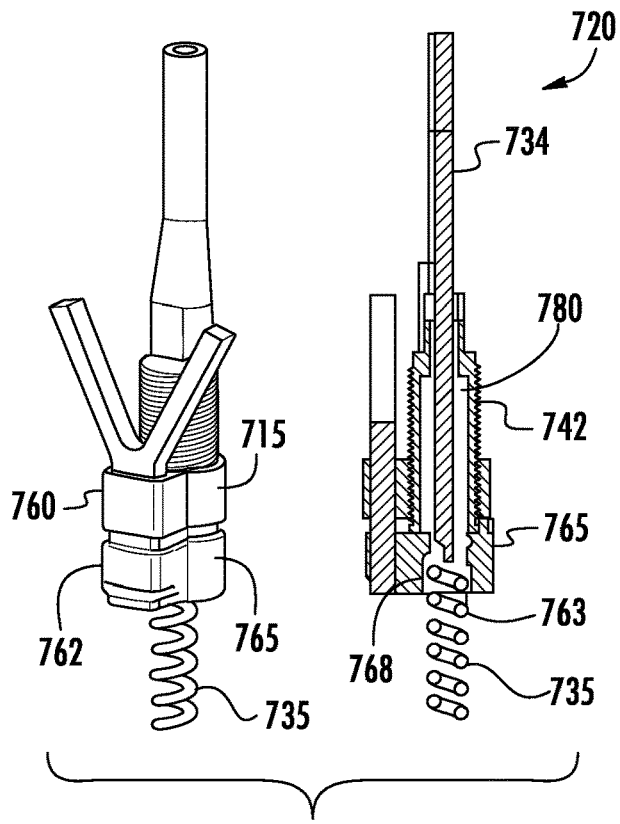
FIGS. 10A-10D illustrate examples of steps of one embodiment of a method for deploying, cinching, and removing implants as disclosed herein.

FIGS. 10A-10D illustrates a portion of a collar based anchor housing assembly 720 as disclosed herein in various stages of delivery. FIG. 10A illustrates a perspective and cross-sectional view as the anchor drive shaft 734 and anchor 735 are distally advanced through the bore 780 of the threaded shaft 742, through the bore 763 of the anchor housing body 765 and into tissue. In one embodiment, rotation of the anchor drive shaft 734 is translated to distal advancement of the anchor 735 at least in part due to grooves 768 disposed within at least a portion of the bore 763 of the anchor housing body 765. When the distal helical portion of the anchor is advanced past the grooves 768 within the bore 763, continued rotation of the anchor driver 730 causes the anchor to free spin within the anchor housing body 765, pulling together the anchor housing body 765 and annular tissue.

Figure 10B:
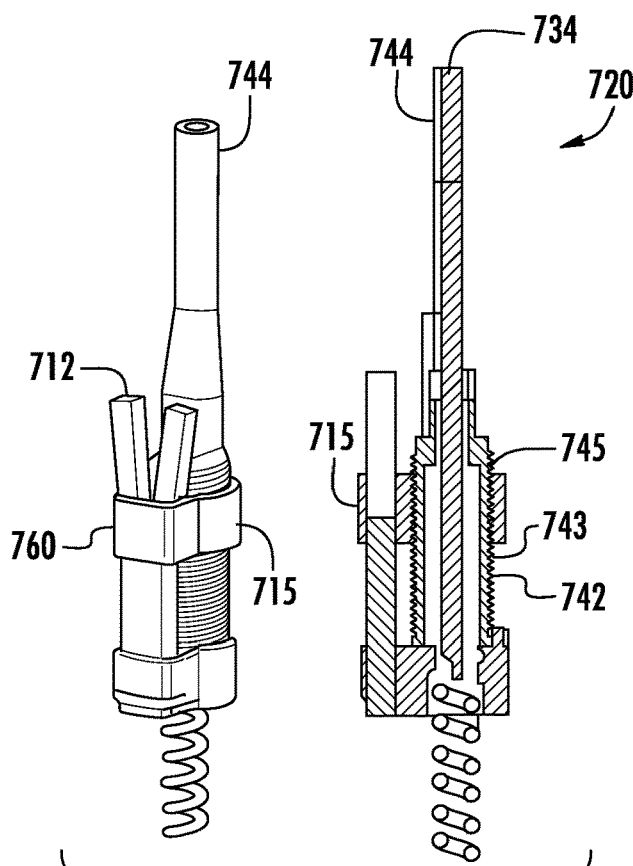

In FIG. 10B, following or concurrently with actuation of the anchor drive shaft 734, the cinch drive tube 744 may be actuated. For example, rotation of the cinch drive tube 744 engages the external threads 743 of the threaded shaft 742 with internal features in the internal bore 745 of the distal collar 715, resulting in translation of the distal collar 715 along the threaded shaft 742. Proximal translation of the distal collar 715 along the threaded shaft 742 causes the struts 712 to be pulled within the sleeve 760 of the distal collar 715, thereby reducing the distance between the struts 712.

Figure 10C:
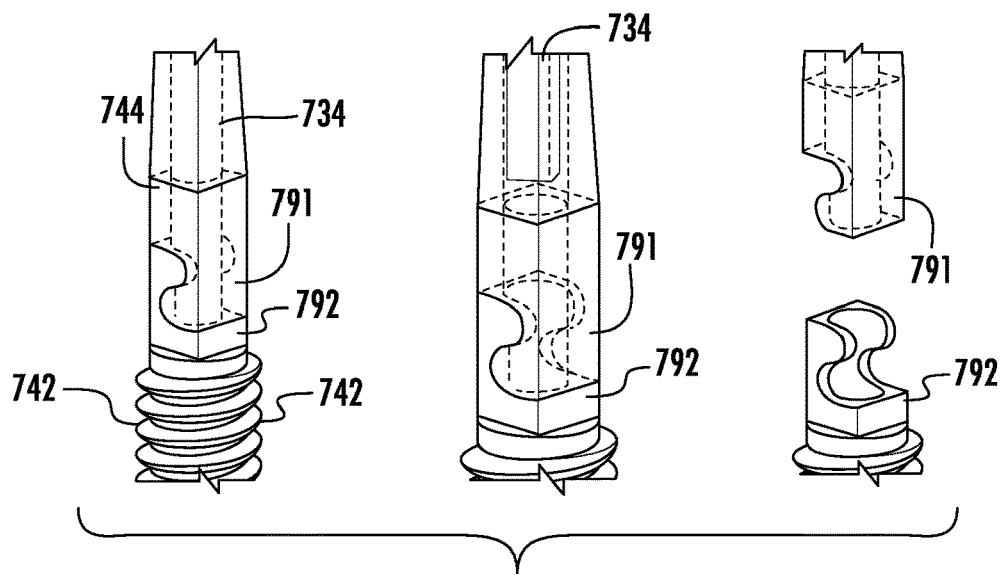

When cinching is completed, as shown in the time lapsed sequence of FIG. 10C, a cinch drive coupler 791 of the cinch drive tube 744 may be removed from a proximal coupler 792 of the threaded shaft 742. In one embodiment, the anchor drive shaft 734 may secure the cinch drive coupler 791 to the proximal coupler 792 of the threaded shaft 742. Removal of the anchor driver 730 from the central axis of the cinch drive tube 744 may release the couplers 791, 792, enabling removal of the cinch drive tube 744 as shown in FIG. 10D.

Figure 10D:
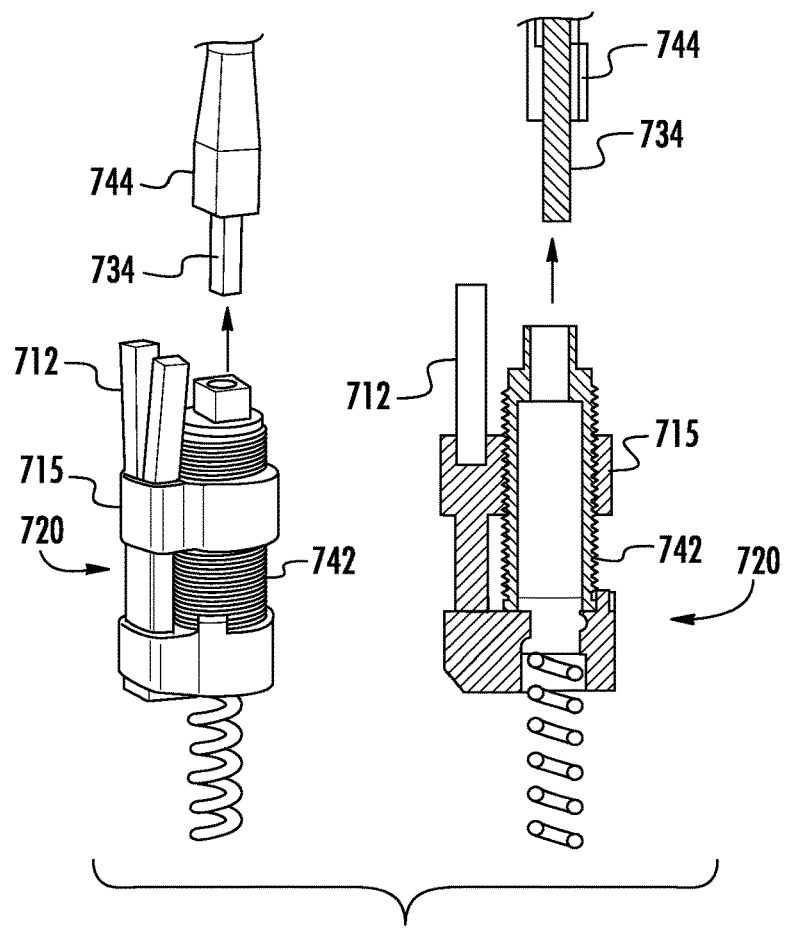

FIG. 10D illustrates removal of the drivers 734, 744 from the anchor housing assembly 720 following cinching and anchoring of the anchor housing assembly 720. The distal collar 715 remains in position about struts 712 and the threaded shaft 742.

Figure 11:
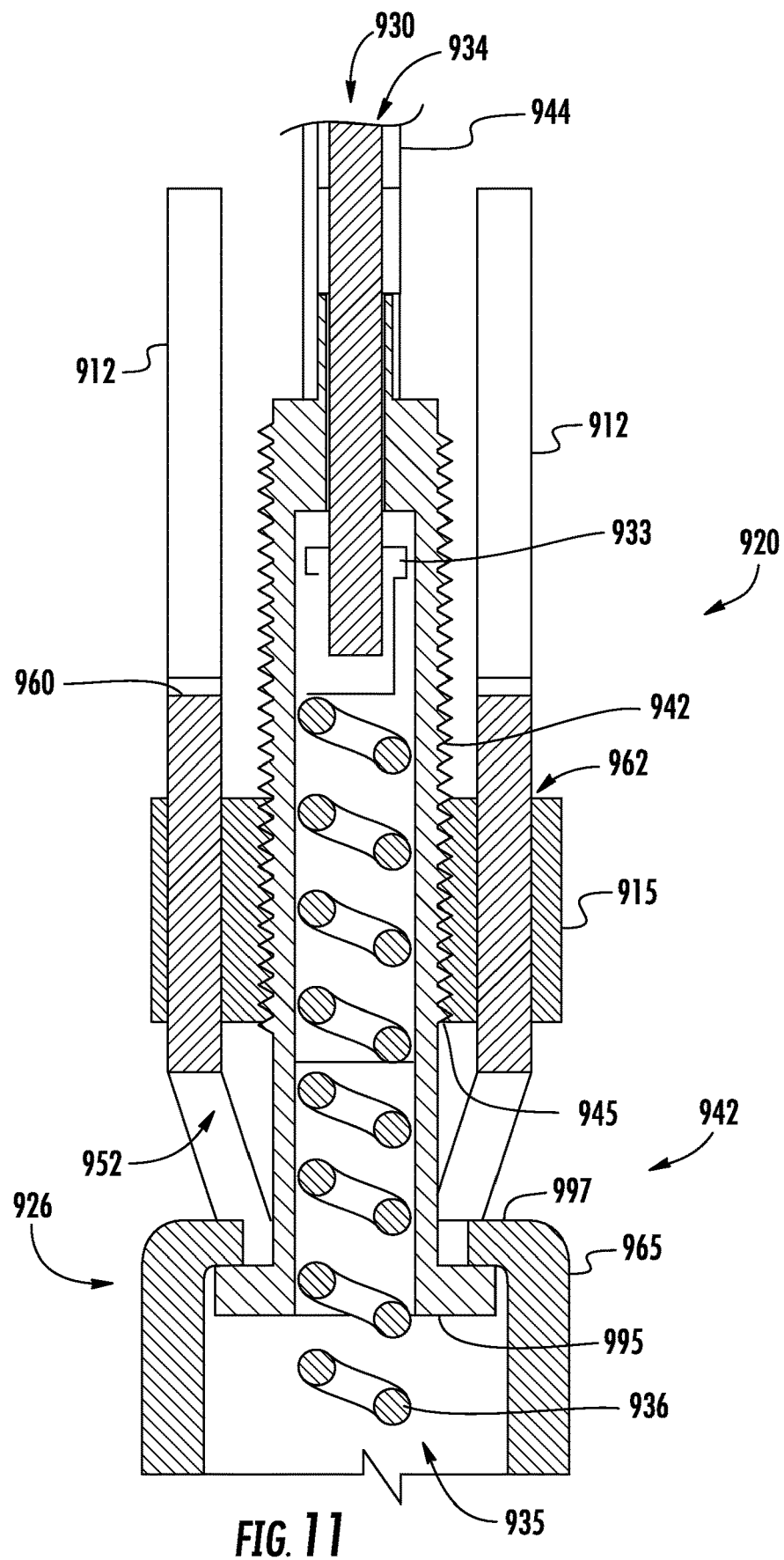
FIG. 11 is a cross-section diagram of one embodiment of a dual sleeve collar based co-axial cinching component as disclosed herein.

FIG. 11 is a cross sectional view of one embodiment of the anchor housing assembly 920. The anchor components 930 of the anchor housing assembly 920 include an anchor drive shaft 934, and an anchor 935, wherein the anchor 935 comprises a proximal coupler 933 and a distal helical portion 936. In one embodiment, the proximal coupler 933 is configured for mated engagement with the anchor drive shaft 934, such that rotation of the anchor drive shaft 934 rotates the anchor 935.

In one embodiment, the threaded shaft 942 includes a bore extending therethrough. The distal collar 915 is disposed about the threaded shaft 942, wherein the distal collar 915 includes an internal bore 945 having internal surface engagement features, such as grooves or complimentary threads, that are configured to interact with the threaded shaft 942 such that rotation of the threaded shaft 942 by a cinch drive tube 944 axially translates the collar 915 over the threaded shaft 942.

In one embodiment, a distal end 926 of the anchor housing assembly 920 includes an anchor housing body 965. In one embodiment, the anchor housing body 965 may include an arm 997 that cooperates with a flange 995 at the distal end of the threaded shaft 942 to secure the threaded shaft 942 with the anchor housing body 965.

In one embodiment, the collar 915 includes a pair of sleeves 960, 962. Each sleeve 960, 962 at least partially surrounds one of the struts 912 of the distal apex 952 of the frame 910, such that proximal translation of the distal collar 915 over the struts 912 of the frame 910 changes the spacing between the struts 912 and pulls together anchor housing assemblies 920.

Figure 12:
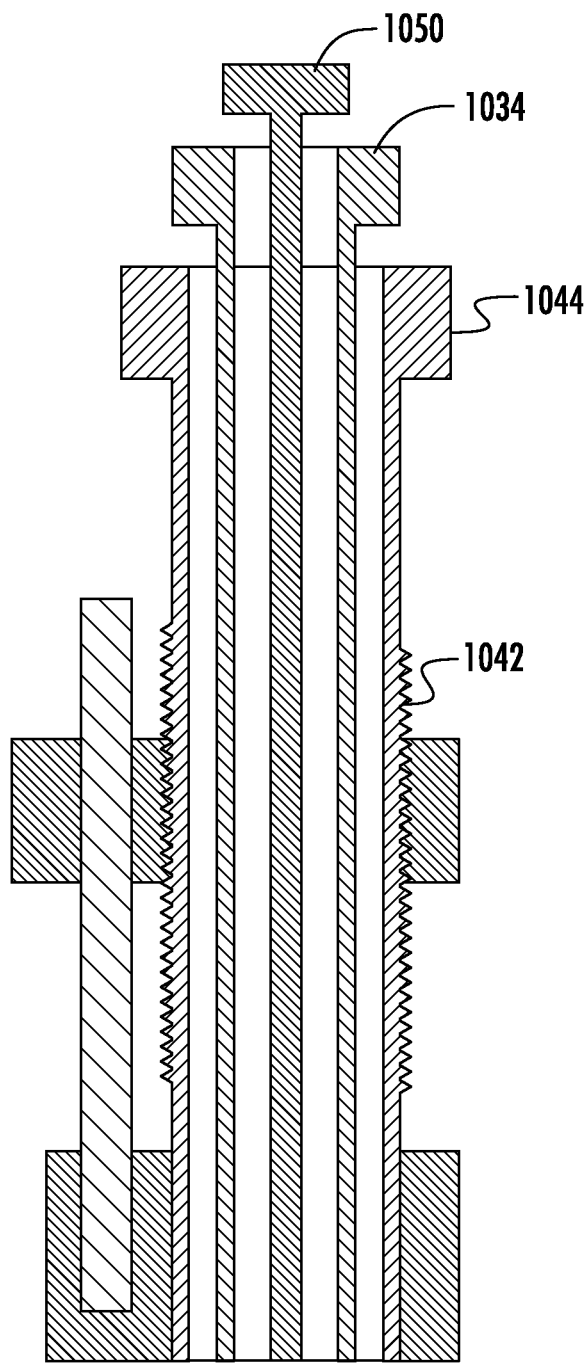
FIG. 12 is a cross section of one embodiment of a coaxial drive shaft comprising a locking pin retention mechanism as disclosed herein.

FIG. 12 is a cross-sectional illustration of a portion of a coaxial anchor housing assembly, including an anchor drive shaft 1034 coaxially aligned within a cinch drive tube 1044 and coupled to a threaded shaft 1042. As described in the embodiment of FIG. 10C, in some delivery systems such as those disclosed herein, the anchor drive tube 1034 may be used to secure the cinch drive tube 1044 to the threaded shaft 1042. In alternate embodiments, such as that of FIG. 11, other mechanisms such as a pin 1050 may be extended through a lumen of the anchor drive shaft 1034, thereby retaining coaxial alignment of the drive shaft 1034 and cinch drive tube 1044 for increased resilience during deployment, and/or to assist interlocking and release.

In various embodiments the anchors disclosed herein, including anchors 135, 735, and 935 may be made of a suitable biocompatible metal alloy such as stainless steel, cobalt chromium, platinum iridium, nickel titanium, other suitable materials, or combinations thereof. Each anchor may be sharpened at its distal point, or leading turn, so as to facilitate penetration into the cardiac tissue (or other tissue to which it is to be anchored). Each anchor may be at least about ten (10) millimeters (mm) and at most about fifteen (15) millimeters (mm) in total axial length. In some embodiments, the anchors may be shorter or longer than ten to fifteen millimeters (mm) in total axial length. By "total" axial length it is meant the axial length of the anchor from the end of the distal penetrating tip to the opposite, proximal coupler. The helical anchor portion of the anchors may be at least about six (6) millimeters (mm) and at most about twelve (12) millimeters (mm) in axial length, i.e., in an axial direction. In some embodiments, the helical portions of the anchor may be shorter or longer than six to twelve millimeters (mm) in axial length. The anchor head and/or other non-helical portions of the anchor may be at least about three (3) millimeters (mm) and at most about four (4) millimeters (mm) in axial length. In some embodiments, the helical diameter range may extend from (0.050"-0.080"), and pitch from (0.030"-0.080"), such that the coil pitch angle is about twenty (20) degrees.

In some embodiments, one or more components of the anchor housing assemblies may be formed from metallic materials and/or polymers with sufficient structural integrity for supporting anchors for driving into the heart annulus. The material may also be chosen based on biocompatibility and fatigue resistance. Material(s) could include stainless steel, Nickel-Titanium, Cobalt-Chromium, Pyrolytic Carbon, Nitinol, polymer materials (e.g., PEEK), and/or other suitable frame materials.

As disclosed in various embodiments herein, in some embodiments the anchor housing assemblies may release the frame following frame positioning, anchoring, and cinching, and in some embodiments the frame may be retained following cinching.

Accordingly, various embodiments of implants comprising anchor housing assemblies including coaxial anchor and cinching components, and associated drive mechanisms, have been shown and described. Although embodiments of the present disclosure may be described with specific reference to medical devices and systems (e.g., transluminal devices inserted through a femoral vein or the like) for selective access to heart tissue, it should be appreciated that such medical devices and systems may be used in a variety of medical procedures that require anchoring to heart tissue. The disclosed medical devices and systems may also be inserted via different access points and approaches, e.g., percutaneously, endoscopically, laparoscopically, or combinations thereof.

As used herein, the singular forms "a," "an," and "the" are intended to include the plural forms as well, unless the context clearly indicates otherwise. The terms "comprises" and/or "comprising," or "includes" and/or "including" when used herein, specify the presence of stated features, regions, steps, elements and/or components, but do not preclude the presence or addition of one or more other features, regions, integers, steps, operations, elements, components, and/or groups thereof.

As used herein, the conjunction "and" includes each of the structures, components, features, or the like, which are so conjoined, unless the context clearly indicates otherwise, and the conjunction "or" includes one or the others of the structures, components, features, or the like, which are so conjoined, singly and in any combination and number, unless the context clearly indicates otherwise.

All numeric values are herein assumed to be modified by the term "about," whether or not explicitly indicated. The term "about," in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified. The recitation of numerical ranges by endpoints includes all numbers within that range, including the endpoints (e.g., 1 to 5 includes 1, 1.5, 2, 2.75, 3, 3.80, 4, and 5).

It is noted that references in the specification to "an embodiment," "some embodiments," "other embodiments," etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described herein, even if not explicitly shown in a particular combination, are nevertheless contemplated as being combinable or arrangeable with each other to form other additional embodiments or to complement and/or enrich the described embodiment(s), as would be understood by one of ordinary skill in the art.

The devices and/or methods disclosed and claimed herein can be made and executed without undue experimentation in light of the present disclosure. While various embodiments of the devices and methods of this disclosure have been described, it may be apparent to those of skill in the art that variations can be applied to the devices and/or methods and in the steps or in the sequence of steps of the method described herein without departing from the concept, spirit, and scope of the disclosure. All such similar substitutes and modifications apparent to those skilled in the art are deemed to be within the spirit, scope, and concept of the disclosure as defined by the appended claims.

What is claimed is:

1. An implant comprising: a pair of anchors, wherein an anchor of the pair of anchors comprises a proximal drive coupler and a distal helical anchor portion; and a pair of anchor housings, wherein at least one of the pair of anchor housings comprises an anchor housing body comprising: an anchoring component configured to translate the anchor along a first axis parallel to a central axis extending proximally-distally through the anchor housing; and a cinch component configured to control a space between the pair of anchor housings; wherein the anchoring component and the cinch component are coaxially mounted.

2. The implant of claim 1, wherein the anchor body of the at least one of the pair of anchor housings has a bore extending along the first axis therethrough, the bore having a bore circumference defined by an inner surface, the inner surface of the bore including a threaded portion configured to axially translate the anchor along the first axis through the bore when a first driving force is applied to the proximal drive coupler of the anchor.

3. The implant of claim 2, wherein the implant comprises a frame having a plurality of struts, a first pair of struts joined at a proximal apex, a second pair of struts joined at a distal apex, and wherein the at least one of the pair of anchor housings is coupled to the frame about the distal apex.

4. The implant of claim 3, wherein the frame is releasably coupled to the at least one of the pair of anchor housings.

5. The implant of claim 3, wherein the cinch component comprises:
 a threaded shaft extending proximally from the at least one of the pair of anchor housings; and
 a collar disposed about the distal apex of the frame and the threaded shaft, the collar configured to axially translate along the threaded shaft and the distal apex in response to rotation of the threaded shaft about the first axis, to modify a strut spacing between the second pair of struts of the distal apex to control the space between the pair of anchor housings.

6. The implant of claim 5, wherein the threaded shaft comprises a shaft bore extending therethrough, the shaft bore axially aligned with the bore of the anchor housing body.

7. The implant of claim 6, wherein a shaft bore circumference exceeds an external diameter of an anchor drive shaft.

8. The implant of claim 5, wherein the collar comprises a first frame sleeve, and wherein the second pair of struts of the distal apex are translatably disposed within the collar.

9. The implant of claim 5, wherein the at least one of the pair of anchor housings comprises a pair of frame sleeves, and wherein one strut of the second pair of struts is translatably disposed in a first sleeve of the pair of frame sleeves and another strut of the second pair of struts is translatably disposed within a second sleeve of the pair of frame sleeves.

10. The implant of claim 5, wherein a distal end of the threaded shaft includes a flange that extends radially from an external surface of the threaded shaft, and the body of the at least one of the pair of anchor housings includes a slot configured to retain the flange of the threaded shaft to secure the threaded shaft to the anchor housing.

11. The implant of claim 3, wherein the cinch component comprises a tether guide and the tether guide comprises a tether lumen extending through the proximal apex of the frame or through the distal apex the frame, and wherein a tether is slidable within the tether lumen to control the space between the pair of anchor housing assemblies.

12. The implant of claim 11, wherein the tether guide of the cinch component comprises a spool, the implant further includes a tether coupled to the spool, and the spool is configured to rotate about a second axis parallel to the central axis to wind or unwind the tether from the spool to control the space between the pair of anchor housings.

13. An implant delivery system comprising:
 an implant comprising:
  a pair of anchors, wherein an anchor of the pair of anchors comprises a proximal drive coupler and a distal helical anchor portion; and
  a pair of anchor housings, wherein at least one of the pair of anchor housings comprises:
   an anchoring component configured to translate the anchor along a first axis parallel to a central axis extending proximally-distally through the anchor housing assembly; and
   a cinch component; and
 a delivery catheter comprising:
  a cinch driver releasably coupled to the cinch component of the at least one of the pair of anchor housings, the cinch driver operable, when actuated, to cause the cinch component to control a space between the pair of anchor housing assemblies, the cinch driver having a cinch driver lumen extending therethrough, the cinch driver lumen parallel to the central axis; and
  an anchor driver releasably coupled to the anchoring component of the at least one of the pair of anchor housings, the anchor driver disposed within the cinch driver lumen.

14. The implant delivery system of claim 13, further including an alignment mechanism configured to maintain coaxial alignment between the cinch component and the anchoring component of the at least one of the pair of anchor housings, the alignment mechanism including a sheath, a pin, or a combination thereof.

15. The implant delivery system of claim 13, wherein the implant further comprises a frame having a plurality of struts, a first pair of struts joined at a proximal apex, a second pair of struts joined at distal ends at a distal apex, and wherein the at least one of the pair of anchor housings is coupled to the frame about the distal apex.

16. The implant delivery system of claim 15, wherein the cinch component of the at least one of the pair of anchor housings further comprises a collar configured to translate axially along the second pair of struts to control the space between the pair of anchor housing assemblies.

17. The implant delivery system of claim 15, wherein the cinch component of the at least one of the pair of anchor housings further comprises a tether and tether guide.

18. The implant delivery system of claim 17, wherein the tether guide comprises a tether lumen extending through the distal apex of the frame, or a rotatable spool, or both.

19. A method of delivering an implant to a valve treatment site, the method comprising: advancing the implant to a treatment site, the implant comprising: a tubular frame comprised of a plurality of sinusoidally joined struts comprising first pairs of struts joined at proximal apices and second pairs of struts joined at distal apices; and a pair of anchor housings, a first anchor housing of the pair of anchor housings coupled to a first distal apex of the tubular frame, a second anchor housing of the pair of anchor housings coupled to a second distal apex of the tubular frame, the first anchor housing comprising an anchor housing body comprising an anchoring component and a cinching component coaxially mounted, a bore extending along a central bore axis disposed proximally-distally through the anchor housing body, and an anchor translationally disposed within the bore; positioning the tubular frame about the valve treatment site; actuating an anchor drive shaft, coupled to the anchoring component of the first anchor housing assembly, to translate the anchor through the bore along the central bore axis into the valve treatment site; and controlling a spacing between anchor housing assemblies using a cinch drive tube that is coaxially disposed about the anchor drive shaft.

20. The method of claim 19, further comprising releasing the tubular frame from the anchor housing assemblies and withdrawing the tubular frame from the valve treatment site.

* * * * *